US00PP20104P2

(12) United States Plant Patent
Bradford

(10) Patent No.: US PP20,104 P2
(45) Date of Patent: Jun. 16, 2009

(54) APRICOT TREE NAMED 'GOLDENMAY'

(50) Latin Name: *Prunus armeniaca*
Varietal Denomination: Goldenmay

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 47 days.

(21) Appl. No.: 12/003,391

(22) Filed: Dec. 26, 2007

(51) Int. Cl.
*A01H 5/00* (2006.01)

(52) U.S. Cl. ..... Plt./186

(58) Field of Classification Search ..... Plt./186
See application file for complete search history.

(56) References Cited

U.S. PATENT DOCUMENTS

PP15,354 P2 11/2004 Bradford

*Primary Examiner*—Annette H Para
*Assistant Examiner*—June Hwu

(57) ABSTRACT

The present invention relates to a new and distinct variety of apricot tree, *Prunus armeniaca,* broadly characterized by a large size, vigorous, hardy, early blooming, self-fertile, productive and regular bearing tree. The fruit matures under the ecological conditions described in late May, with first picking on May 18, 2007. The fruit is uniformly large in size, mildly acidic and sweet in flavor, globose in shape, freestone in type, firm and meaty in texture, orange in flesh color, and orange skin color.

1 Drawing Sheet

Botanical classification: *Prunus armeniaca.*
Variety denomination: 'GOLDENMAY'.

BACKGROUND OF THE VARIETY

In a continuing effort to improve the quality of shipping fruits, I, the inventor, typically hybridize a large number of apricot, nectarine, plum, apricot, and cherry seedlings each year. I also grow a lesser number of open pollinated seeds of each of these fruits, usually to capture recessive traits. The present invention relates to a new and distinct variety of apricot tree, which has been denominated varietally as 'Goldenmay'.

The present variety was hybridized by me in 2000 as a first generation cross using 'Goldenblush' (U.S. Plant Pat. No. 15,354) apricot as the selected seed parent and '16P245' (unpatented) apricot as the selected pollen parent. The fruit of this cross was gathered that spring, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2004 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, 'Goldenblush' (U.S. Plant Pat. No. 15,354) apricot by blooming in the early season and by producing apricots that are freestone in type, orange in skin and flesh color, and mature in late May, but is distinguished therefrom by being self-fruitful, more productive, and by producing fruit that is larger in size, that is not as sweet in flavor, that has a much less pronounced suture, and that does not have red blush on the skin.

The present variety is similar to its pollen parent, '16P245,' by producing fruit that ripens in the early season and that is good in flavor, but is distinguished therefrom by being self-fruitful, by being more productive, and by producing fruit that is firmer in texture.

The present variety is similar to 'Castlebrite' (unpatented) apricot by being self-fruitful and producing fruit that matures in the early season, but is distinguished therefrom by requiring much less chilling and by producing fruit that is larger in size and much lower in acidity.

SUMMARY OF VARIETY

In summary, the present variety is characterized by a large size, vigorous, hardy, early blooming, self-fertile, productive and regular bearing tree. The fruit matures under the ecological conditions described in late May, with first picking on May 18, 2007. The fruit is uniformly large in size, mildly acidic and sweet in flavor, globose in shape, freestone in type, firm and meaty in texture, orange in flesh color, and orange skin color.

DRAWING

The accompanying photograph consists of four whole fruits positioned to display the characteristics of the skin color and form, one fruit divided to reveal the flesh and stone, typical leaves, a tip shoot, and three insets showing buds and blossoms.

POMOLOGICAL CHARACTERISTICS

Referring now more specifically to the pomological characteristics of this new and distinct variety of apricot tree, the following has been observed under the ecological conditions prevailing near Le Grand, Merced County (San Joaquin Valley), Calif., and was developed at the state of firm ripe on May 28, 2007, on the original tree during its seventh growing season. The blossom and flower descriptions were made the previous blooming season. All major color code designations are by reference to the Inter-Society Color Council, National Bureau of Standards. Common color names are also used occasionally.

Parentage

Seed Parent: 'Goldenblush' (U.S. Plant Pat. No. 15,354) apricot.
Pollen Color.—Yellow.
Pollen Parent: '16P245' (unpatented) apricot.

Tree

Size: Large, reaching and maintaining a height of 12' [3.66 m.] and a spread of 9' [2.74 m.] after seven growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase type.
Hardiness: Hardy with respect to central California winters.
Heat Tolerance: Observed to perform adequately in typical central California climatic conditions, which typically include extended periods of heat.
Drought Tolerance: Variety is developed for commercial orchards and requires regular irrigation.
Production: Very productive, thinning necessary.
Fertility: Self-fertile.
Bearing: Regular bearer with no alternate bearing yet observed.
Trunk:
*Size.*—Medium, reaching a maximum diameter of 4¼" [108 mm.] after the seventh growing season.
*Texture.*—Shaggy.
*Bark color.*—A Grayish brown [61. gy.Br] and Light grayish brown [60. l.gy.Br] variegation with Light yellowish brown [76. l.yBr] crevices present.
*Lenticels.*—Approximate Number Per Square Inch: 7. Color: Light yellowish brown [76. l.yBr]. Average Size: 3/16" [4.8 mm.]. Shape: Eye-shaped, elongated.
Branches:
*Size.*—Diameter of limb is 2¼" [57 mm.] measured 12" above the crotch, 1¼" [32 mm.] measured 12" above the first fork.
*Texture.*—Smooth on first and second year wood, increasing roughness with age.
*Color.*—1st Year Wood Topside: Strong yellow green [117. s.YG]. 1st Year Wood Underside: Brownish orange [54. brO]. Older Wood: Deep yellowish brown [75. deep yBr].
*Lenticels.*—Number Per Square Inch: More than 30 on second year wood. Color: Light orange yellow [70. l.OY]. Average size: 1/32" [0.8 mm.] on second year wood. Shape: Rectangular, elongated.
Leaves:
*Size.*—Medium. Average Length: 2¾" [69.9 mm.]. Average Width: 2⅜" [60.3 mm.].
*Arrangement.*—Alternate.
*Thickness.*—Medium.
*Form.*—Oval to orbicular.
*Apex.*—Abruptly acuminate.
*Base.*—Rounded.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Vein color.*—Light yellow green [119. l.YG].
*Petiole.*—Average Length: 1 1/16" [27 mm.]. Average Thickness: 1/16" [1.6 mm.]. Color: Strong reddish brown [40. s.rBr] topside, Light yellow green [119. l.YG] underneath.
*Stipules.*—Number: Usually 2 per leaf, up to 6 per growing tip. Average Length: ¼" [6.4 mm.]. Color: Very yellow green [115. v.YG] becoming Deep reddish brown [41. deep rBr] with maturity.
*Glands.*—Number: 2 to 3 per leaf. Position: Alternately positioned on petiole and base of blade. Size: Small. Form: Globose. Color: Strong reddish brown [40. s.rBr] becoming Dark reddish brown [44. d.rBr] with age.
*Leaf buds.*—Pointed, medium in size.
Flower Buds:
*Hardiness.*—Half-hardy, with respect to central California winters.
*Diameter.*—Typically 5/16" [7.9 mm.] 5 days before bloom.
*Length.*—Typically ⅜" [9.5 mm.] 5 days before bloom.
*Form.*—Not appressed.
*Surface.*—Pubescent.
*Color.*—Pale purplish pink [252. p.pPk].
Flowers: Perfect, complete, perigynous, usually a single pistil, typically twenty-four or more stamens, five sepals and petal locations alternately positioned.
*Average flower diameter.*1—⅜" [34.9 mm.].
*Number of petals.*—Usually five.
*Petal shape.*—Circular to elliptical.
*Petal margin.*—Entire, fairly smooth.
*Average petal diameter.*—9/16" [14.3 mm.].
*Average petal length.*—9/16" [14.3 mm.].
*Petal apex.*—Rounded.
*Petal base.*—Rounded.
*Petal color.*—Pinkish white [9. pkWhite] on both sides.
*Anther color.*—Brilliant yellow [83. brill.Y].
*Stigma color.*—Light greenish yellow [101. l.gY].
*Sepal color.*—Deep purplish red [256. deep pR] on the outer surface.
*Sepal length.*—9/32" [7.1 mm.].
*Sepal width.*—3/16" [4.8 mm.].
*Sepal apex.*—Acute to acuminate.
*Sepal margin.*—Smooth.
*Average pistil length.*—½" [12.7 mm.].
*Average stamen length.*—7/16" [11.1 mm.].
*Fragrance.*—Moderate.
*Pollen Production.*—Abundant.
*Blooming period.*—Early compared to other apricots, with 'Goldenblush' (U.S. Plant Pat. No. 15,354).
*Onset of bloom.*—One percent on Feb. 20, 2007.
*Date of full bloom.*—Feb. 27, 2007.
*Duration of bloom.*—One to two weeks, dependent on ambient temperature.
*Average number per cluster.*—Three.

FRUIT

Maturity when described: Firm ripe, May 28, 2007.
Date of first picking: May 21, 2007.
Date of last picking: May 30, 2007.

Size: Uniform, Large.
*Average diameter axially.*—2¼ [57.2 mm.].
*Average diameter across suture plane.*—2⅝" [66.7 mm.].
*Typical weight.*—4.3 ounces [122 grams].
Form: Uniform, globose, symmetrical.
*Longitudinal section form.*—Round to elliptical.
*Transverse section through diameter.*—Round.
Suture: Extends from the base, along the side, to just beyond the pistil point.
*Near the base.*—A very shallow groove.
*Along the side.*—An indistinct line.
*Near the apex.*—A shallow trough with a minor depression just past the pistil point.
Ventral surface: Rounded, lipped toward the apex.
Lips: Equal.
Cavity: Flaring, circular, suture showing on one side.
*Depth.*—⅜" [9.5 mm.].
*Breadth.*—15/16" [23.8 mm.].
Base: Rounded to truncate.
Apex: Rounded.
Pistil point: Apical, negligible in length, recessed within the suture.
Stem: Medium.
*Average length.*—5/16"[7.9 mm.].
*Average width.*—1/16"[1.6 mm.].
Skin:
*Thickness.*—Medium.
*Surface.*—Smooth.
*Tenacity.*—Tenacious to flesh.
*Astringency.*—Slightly astringent.
*Tendency to crack.*—None observed in dry season.
*Color.*—Moderate reddish orange [37. m.rO] smoothly blending into a Strong orange [50. s.O] background.
Flesh:
*Color.*—Strong orange yellow [68. s.OY] becoming Very orange [48. v.O] with increasing maturity.
*Surface of pit cavity.*—Covered with Light orange yellow [70. l.OY] fibers.
*Amygdalin.*—Moderate.
*Juice.*—Moderate, rich.
*Texture.*—Firm, meaty, melting.
*Fibers.*—Few, fine, tender.
*Ripens.*—Even.
*Flavor.*—A mild balance of acid and sugar, typically 15 brix.
*Aroma.*—Moderate.
*Eating quality.*—Good.

STONE

Type: Freestone.
Form: Oval.
Hilum: Narrow, oblong.
Base: Rounded, cupped at the hilum.
Apex: Obtuse with a 1/16" [1.6 mm.] tip having an average angle of 70 degrees.
Sides: Equal.
Surface: Rough throughout.
External color of stone: Dark yellowish brown [78. d.yBr].
Pit wall color when cracked: Deep yellowish brown [75. deep yBr].
Cavity surface color: A Pale orange yellow [73. p.OY] and Light yellowish brown [76. l.yBr] variegation.
Average pit wall thickness: 1/16" [1.6 mm.].
Average width: 1" [25.4 mm.].
Average length: 1 3/16" [30.2 mm.].
Average breadth: ½" [12.7 mm.].
Tendency to split: Very slight.
Kernel:
*Form.*—Oval.
*Skin color.*—Light orange yellow [70. l.OY] when first remove.
*Pellicle color.*—Moderate orange yellow [71. m.OY].
*Taste.*—Bitter.
*Viable.*—Yes.
*Average width.*—⅝" [15.9 mm.].
*Average length.*⅞" [22.2 mm.].
*Amygdalin.*—Abundant.

Use

Market: Fresh market and long distance shipping.
Keeping quality: Good, fruit quality observed to remain in good condition after 14 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of apricot tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of apricot tree, substantially as illustrated and described, that is similar to its seed parent, 'Goldenblush' U.S. Plant Pat. No. 15,354) apricot, by blooming in the early season and by producing apricots that are freestone in type, orange in flesh and skin color, and mature in late May, but is distinguished therefrom by being self-fruitful, more productive, and by producing fruit that is larger in size, that is not as sweet in flavor, that has a much less pronounced suture, and that does not have red blush on the skin.

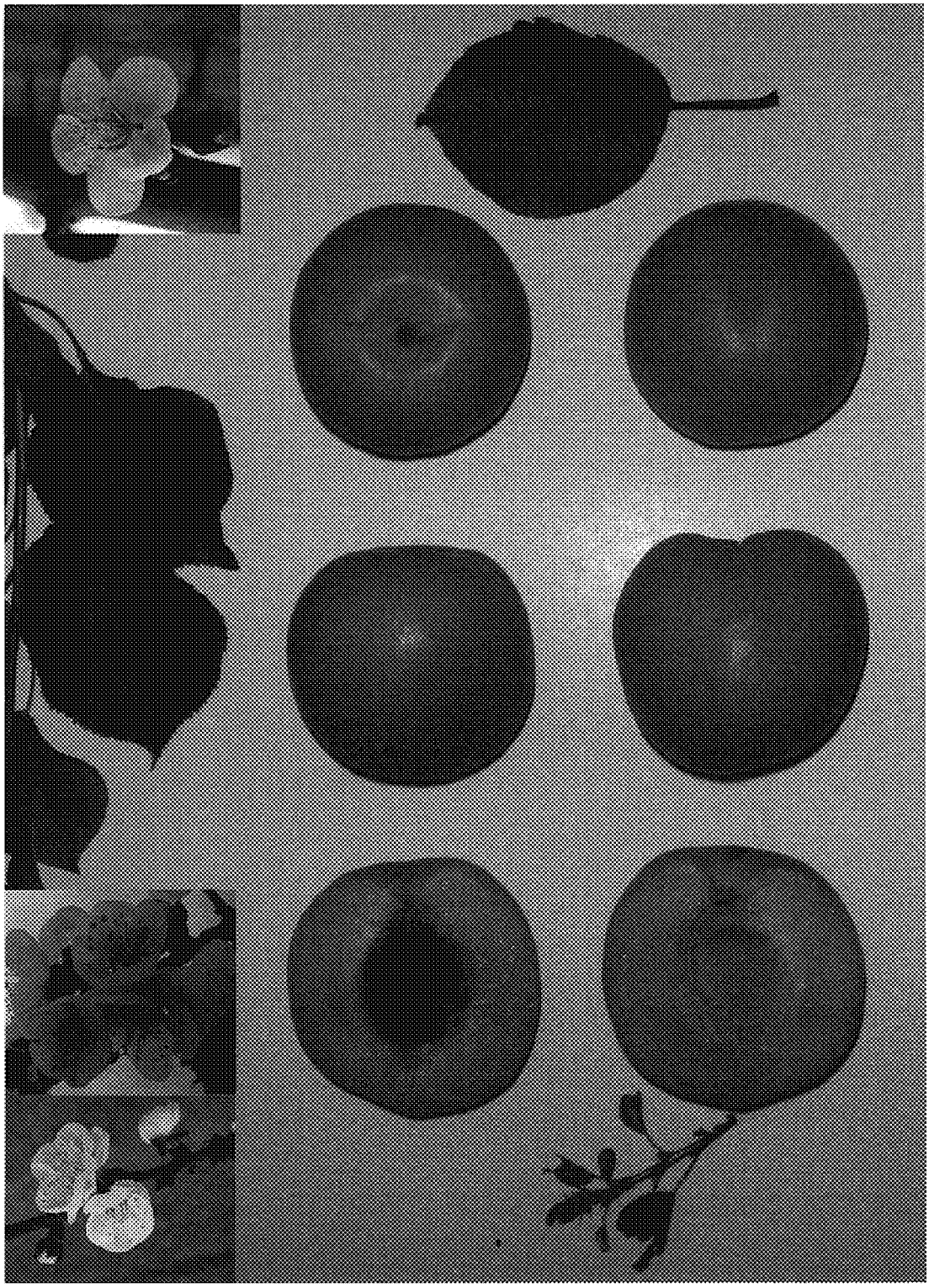

* * * * *